(12) United States Patent
Kostrzewski et al.

(10) Patent No.: US 11,284,893 B2
(45) Date of Patent: Mar. 29, 2022

(54) STAPLING DEVICE WITH ARTICULATING TOOL ASSEMBLY

(71) Applicant: Covidien LP, Mansfield, MA (US)

(72) Inventors: Stanislaw Kostrzewski, Newtown, CT (US); John Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 23 days.

(21) Appl. No.: 16/806,077

(22) Filed: Mar. 2, 2020

(65) Prior Publication Data

US 2020/0315622 A1  Oct. 8, 2020

Related U.S. Application Data

(60) Provisional application No. 62/828,217, filed on Apr. 2, 2019.

(51) Int. Cl.
  *A61B 17/072* (2006.01)
  *A61B 17/00* (2006.01)
  *A61B 17/29* (2006.01)

(52) U.S. Cl.
  CPC .... *A61B 17/072* (2013.01); *A61B 2017/0053* (2013.01); *A61B 2017/07257* (2013.01);
  (Continued)

(58) Field of Classification Search
  CPC ............ A61B 17/072; A61B 17/07207; A61B 17/105; A61B 17/115; A61B 17/2816;
  (Continued)

(56) References Cited

U.S. PATENT DOCUMENTS 3,499,591 A  3/1970  Green
3,777,538 A  12/1973  Weatherly et al.
(Continued)

FOREIGN PATENT DOCUMENTS

AU  198654765  9/1986
CA  2773414 A1  11/2012
(Continued)

OTHER PUBLICATIONS

European Search Report dated Aug. 28, 2020, issued in EP Appln. No. 20166542, 10 pages.
(Continued)

*Primary Examiner* — Stephen F. Gerrity
*Assistant Examiner* — Linda J Hodge

(57) ABSTRACT

A surgical stapling device includes a mounting assembly that is pivotably supported on a distal portion of a housing about a pivot axis and movable between a non-articulated position and an articulated position. A drive assembly includes a flexible body having a working end and an articulation assembly includes an active articulation link that is coupled to the mounting assembly and movable between a retracted position and an advanced position to pivot the mounting assembly about the pivot axis. A gate assembly defines a channel that receives the flexible body of the drive assembly. The active articulation link is positioned to engage the gate assembly when the active articulation link moves between its retracted and advanced positions to move the gate assembly to a position to increase the bending radius of the flexible body of the drive assembly.

17 Claims, 12 Drawing Sheets

(52) U.S. Cl.
CPC .............. *A61B 2017/07271* (2013.01); *A61B 2017/2927* (2013.01)

(58) Field of Classification Search
CPC ........... A61B 2017/07228; A61B 2017/07257; A61B 2017/07271; A61B 2017/07285; A61B 2017/0053; A61B 2017/2927; A61B 2017/00473; A61B 2017/07214; A61B 2017/00367; A61B 2017/00477
See application file for complete search history.

(56) References Cited

U.S. PATENT DOCUMENTS

| | | |
|---|---|---|
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |

(56) References Cited

U.S. PATENT DOCUMENTS

| | | |
|---|---|---|
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Billner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Mien et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |

(56) References Cited

U.S. PATENT DOCUMENTS

| | | |
|---|---|---|
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |

(56) References Cited

U.S. PATENT DOCUMENTS

| | | |
|---|---|---|
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |

(56) References Cited

U.S. PATENT DOCUMENTS

| | | |
|---|---|---|
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |

(56) References Cited

U.S. PATENT DOCUMENTS

| | | |
|---|---|---|
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |

(56) References Cited

U.S. PATENT DOCUMENTS

| | | | |
|---|---|---|---|
| 8,573,461 | B2 | 11/2013 | Shelton, IV et al. |
| 8,573,463 | B2 | 11/2013 | Scirica et al. |
| 8,573,465 | B2 | 11/2013 | Shelton, IV |
| 8,579,176 | B2 | 11/2013 | Smith et al. |
| 8,579,177 | B2 | 11/2013 | Beetel |
| 8,584,919 | B2 | 11/2013 | Hueil et al. |
| 8,584,920 | B2 | 11/2013 | Hodgkinson |
| 8,590,762 | B2 | 11/2013 | Hess et al. |
| 8,596,515 | B2 | 12/2013 | Okoniewski |
| 8,602,288 | B2 | 12/2013 | Shelton, IV et al. |
| 8,608,045 | B2 | 12/2013 | Smith et al. |
| 8,608,046 | B2 | 12/2013 | Laurent et al. |
| 8,608,047 | B2 | 12/2013 | Holsten et al. |
| 8,613,383 | B2 | 12/2013 | Beckman et al. |
| 8,613,384 | B2 | 12/2013 | Pastorelli et al. |
| 8,616,427 | B2 | 12/2013 | Viola |
| 8,616,430 | B2 | 12/2013 | Stopek et al. |
| 8,627,994 | B2 | 1/2014 | Zemlok et al. |
| 8,628,544 | B2 | 1/2014 | Farascioni |
| 8,631,988 | B2 | 1/2014 | Viola |
| 8,631,989 | B2 | 1/2014 | Aranyi et al. |
| 8,631,991 | B2 | 1/2014 | Cropper et al. |
| 8,632,525 | B2 | 1/2014 | Kerr et al. |
| 8,632,535 | B2 | 1/2014 | Shelton, IV et al. |
| 8,636,187 | B2 | 1/2014 | Hueil et al. |
| 8,636,190 | B2 | 1/2014 | Zemlok et al. |
| 8,636,192 | B2 | 1/2014 | Farascioni et al. |
| 8,636,762 | B2 | 1/2014 | Whitman et al. |
| 8,636,766 | B2 | 1/2014 | Milliman et al. |
| 8,640,940 | B2 | 2/2014 | Ohdaira |
| 8,657,174 | B2 | 2/2014 | Yates et al. |
| 8,657,177 | B2 | 2/2014 | Scirica et al. |
| 8,657,178 | B2 | 2/2014 | Hueil et al. |
| 8,662,371 | B2 | 3/2014 | Viola |
| 8,668,129 | B2 | 3/2014 | Olson |
| 8,672,206 | B2 | 3/2014 | Aranyi et al. |
| 8,672,208 | B2 | 3/2014 | Hess et al. |
| 8,672,209 | B2 | 3/2014 | Crainich |
| 8,678,263 | B2 | 3/2014 | Viola |
| 8,678,990 | B2 | 3/2014 | Wazer et al. |
| 8,679,155 | B2 | 3/2014 | Knodel et al. |
| 8,684,247 | B2 | 4/2014 | Scirica et al. |
| 8,684,249 | B2 | 4/2014 | Racenet et al. |
| 8,684,253 | B2 | 4/2014 | Giordano et al. |
| 8,690,039 | B2 | 4/2014 | Beardsley et al. |
| 8,695,865 | B2 | 4/2014 | Smith et al. |
| 8,695,866 | B2 | 4/2014 | Leimbach et al. |
| 8,701,958 | B2 | 4/2014 | Shelton, IV et al. |
| 8,701,959 | B2 | 4/2014 | Shah |
| 8,701,961 | B2 | 4/2014 | Ivanko |
| 8,708,213 | B2 | 4/2014 | Shelton, IV et al. |
| 8,714,429 | B2 | 5/2014 | Demmy |
| 8,715,277 | B2 | 5/2014 | Weizman |
| 8,720,766 | B2 | 5/2014 | Hess et al. |
| 8,721,630 | B2 | 5/2014 | Ortiz et al. |
| 8,727,197 | B2 | 5/2014 | Hess et al. |
| 8,727,200 | B2 | 5/2014 | Roy |
| 8,733,612 | B2 | 5/2014 | Ma |
| 8,740,034 | B2 | 6/2014 | Morgan et al. |
| 8,740,039 | B2 | 6/2014 | Farascioni |
| 8,746,529 | B2 | 6/2014 | Shelton, IV et al. |
| 8,746,530 | B2 | 6/2014 | Giordano et al. |
| 8,746,535 | B2 | 6/2014 | Shelton, IV et al. |
| 8,752,748 | B2 | 6/2014 | Whitman et al. |
| 8,752,749 | B2 | 6/2014 | Moore et al. |
| 8,757,465 | B2 | 6/2014 | Woodard, Jr. et al. |
| 8,758,391 | B2 | 6/2014 | Swayze et al. |
| 8,763,877 | B2 | 7/2014 | Schall et al. |
| 8,763,879 | B2 | 7/2014 | Shelton, IV et al. |
| 8,770,458 | B2 | 7/2014 | Scirica |
| 8,777,082 | B2 | 7/2014 | Scirica |
| 8,783,541 | B2 | 7/2014 | Shelton, IV et al. |
| 8,783,542 | B2 | 7/2014 | Riestenberg et al. |
| 8,789,737 | B2 | 7/2014 | Hodgkinson et al. |
| 8,789,738 | B2 | 7/2014 | Knodel et al. |
| 8,789,739 | B2 | 7/2014 | Swensgard |
| 8,800,838 | B2 | 8/2014 | Shelton, IV |
| 8,800,840 | B2 | 8/2014 | Jankowski |
| 8,800,841 | B2 | 8/2014 | Ellerhorst et al. |
| 8,808,311 | B2 | 8/2014 | Heinrich et al. |
| 8,814,024 | B2 | 8/2014 | Woodard, Jr. et al. |
| 8,814,025 | B2 | 8/2014 | Miller et al. |
| 8,820,603 | B2 | 9/2014 | Shelton, IV et al. |
| 8,820,605 | B2 | 9/2014 | Shelton, IV |
| 8,820,607 | B2 | 9/2014 | Marczyk |
| 8,827,133 | B2 | 9/2014 | Shelton, IV et al. |
| 8,827,134 | B2 | 9/2014 | Viola et al. |
| 8,833,631 | B2 | 9/2014 | Munro, III et al. |
| 8,833,632 | B2 | 9/2014 | Swensgard |
| 8,840,003 | B2 | 9/2014 | Morgan et al. |
| 8,840,603 | B2 | 9/2014 | Shelton, IV et al. |
| 8,844,788 | B2 | 9/2014 | Knodel |
| 8,851,354 | B2 | 10/2014 | Swensgard et al. |
| 8,851,355 | B2 | 10/2014 | Aranyi et al. |
| 8,857,693 | B2 | 10/2014 | Schuckmann et al. |
| 8,864,007 | B2 | 10/2014 | Widenhouse et al. |
| 8,864,009 | B2 | 10/2014 | Shelton, IV et al. |
| 8,875,971 | B2 | 11/2014 | Hall et al. |
| 8,875,972 | B2 | 11/2014 | Weisenburgh, II et al. |
| 8,893,949 | B2 | 11/2014 | Shelton, IV et al. |
| 8,893,950 | B2 | 11/2014 | Marczyk |
| 8,899,461 | B2 | 12/2014 | Farascioni |
| 8,899,463 | B2 | 12/2014 | Schall et al. |
| 8,899,464 | B2 | 12/2014 | Hueil et al. |
| 8,900,616 | B2 | 12/2014 | Belcheva et al. |
| 8,920,435 | B2 | 12/2014 | Smith et al. |
| 8,925,782 | B2 | 1/2015 | Shelton, IV |
| 8,926,598 | B2 | 1/2015 | Mollere et al. |
| 8,931,682 | B2 | 1/2015 | Timm et al. |
| 8,931,693 | B1 | 1/2015 | Kumar et al. |
| 8,955,732 | B2 | 2/2015 | Zemlok et al. |
| 8,958,429 | B2 | 2/2015 | Shukla et al. |
| 8,960,517 | B2 | 2/2015 | Lee |
| 8,967,443 | B2 | 3/2015 | McCuen |
| 8,967,446 | B2 | 3/2015 | Beardsley et al. |
| 8,973,803 | B2 | 3/2015 | Hall et al. |
| 8,978,954 | B2 | 3/2015 | Shelton, IV et al. |
| 8,978,956 | B2 | 3/2015 | Schall et al. |
| 8,998,060 | B2 | 4/2015 | Bruewer et al. |
| 9,005,230 | B2 | 4/2015 | Yates et al. |
| 9,010,607 | B2 | 4/2015 | Kostrzewski |
| 9,016,539 | B2 | 4/2015 | Kostrzewski et al. |
| 9,016,541 | B2 | 4/2015 | Viola et al. |
| 9,016,542 | B2 | 4/2015 | Shelton, IV et al. |
| 9,016,546 | B2 | 4/2015 | Demmy et al. |
| 9,022,271 | B2 | 5/2015 | Scirica |
| 9,027,817 | B2 | 5/2015 | Milliman et al. |
| 9,033,203 | B2 | 5/2015 | Woodard, Jr. et al. |
| 9,044,228 | B2 | 6/2015 | Woodard, Jr. et al. |
| 9,044,229 | B2 | 6/2015 | Scheib et al. |
| 9,050,084 | B2 | 6/2015 | Schmid et al. |
| 9,055,941 | B2 | 6/2015 | Schmid et al. |
| 9,060,770 | B2 | 6/2015 | Shelton, IV et al. |
| 9,072,535 | B2 | 7/2015 | Shelton, IV et al. |
| 9,089,326 | B2 | 7/2015 | Krumanaker et al. |
| 9,101,359 | B2 | 8/2015 | Smith et al. |
| 9,107,663 | B2 | 8/2015 | Swensgard |
| 9,107,664 | B2 | 8/2015 | Marczyk |
| 9,113,862 | B2 | 8/2015 | Morgan et al. |
| 9,113,864 | B2 | 8/2015 | Morgan et al. |
| 9,113,870 | B2 | 8/2015 | Viola |
| 9,113,872 | B2 | 8/2015 | Viola |
| 9,113,880 | B2 | 8/2015 | Zemlok et al. |
| 9,125,649 | B2 | 9/2015 | Bruewer et al. |
| 9,138,225 | B2 | 9/2015 | Huang et al. |
| 9,155,537 | B2 | 10/2015 | Katre et al. |
| 9,179,912 | B2 | 11/2015 | Yates et al. |
| 9,192,378 | B2 | 11/2015 | Aranyi et al. |
| 9,192,379 | B2 | 11/2015 | Aranyi et al. |
| 9,192,384 | B2 | 11/2015 | Bettuchi |
| 9,198,644 | B2 | 12/2015 | Balek et al. |
| 9,198,661 | B2 | 12/2015 | Swensgard |
| 9,204,876 | B2 | 12/2015 | Cappola et al. |
| 9,216,019 | B2 | 12/2015 | Schmid et al. |

(56) References Cited

U.S. PATENT DOCUMENTS

| | | |
|---|---|---|
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0051669 A1 | 3/2010 | Milliman |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |

(56) References Cited

U.S. PATENT DOCUMENTS

| | | |
|---|---|---|
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0186929 A1* | 7/2013 | Williams ......... A61B 17/07207 227/175.1 |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0230793 A1* | 8/2015 | Kostrzewski ...... A61B 17/0644 227/176.1 |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |

(56) References Cited

U.S. PATENT DOCUMENTS

| | | | |
|---|---|---|---|
| 2016/0113648 A1 | 4/2016 | Zergiebel et al. | |
| 2016/0113649 A1 | 4/2016 | Zergiebel et al. | |
| 2016/0120542 A1 | 5/2016 | Westling et al. | |
| 2016/0166249 A1 | 6/2016 | Knodel | |
| 2016/0166253 A1 | 6/2016 | Knodel | |
| 2016/0174972 A1* | 6/2016 | Shelton, IV | A61B 17/105 227/180.1 |
| 2016/0199064 A1 | 7/2016 | Shelton, IV et al. | |
| 2016/0199084 A1 | 7/2016 | Takei | |
| 2016/0206315 A1 | 7/2016 | Olson | |
| 2016/0206336 A1 | 7/2016 | Frushour | |
| 2016/0235494 A1 | 8/2016 | Shelton, IV et al. | |
| 2016/0242773 A1 | 8/2016 | Sadowski et al. | |
| 2016/0242774 A1 | 8/2016 | Ebner | |
| 2016/0242779 A1 | 8/2016 | Aranyi et al. | |
| 2016/0249915 A1 | 9/2016 | Beckman et al. | |
| 2016/0249916 A1 | 9/2016 | Shelton, IV et al. | |
| 2016/0249918 A1 | 9/2016 | Shelton, IV et al. | |
| 2016/0249927 A1 | 9/2016 | Beckman et al. | |
| 2016/0249929 A1 | 9/2016 | Cappola et al. | |
| 2016/0249945 A1 | 9/2016 | Shelton, IV et al. | |
| 2016/0256071 A1 | 9/2016 | Shelton, IV et al. | |
| 2016/0256152 A1 | 9/2016 | Kostrzewski | |
| 2016/0256154 A1 | 9/2016 | Shelton, IV et al. | |
| 2016/0256160 A1 | 9/2016 | Shelton, IV et al. | |
| 2016/0256161 A1 | 9/2016 | Overmyer et al. | |
| 2016/0256162 A1 | 9/2016 | Shelton, IV et al. | |
| 2016/0256163 A1 | 9/2016 | Shelton, IV et al. | |
| 2016/0256184 A1 | 9/2016 | Shelton, IV et al. | |
| 2016/0256185 A1 | 9/2016 | Shelton, IV et al. | |
| 2016/0256187 A1 | 9/2016 | Shelton, IV et al. | |
| 2016/0262750 A1 | 9/2016 | Hausen et al. | |
| 2016/0270783 A1 | 9/2016 | Yigit et al. | |
| 2016/0270788 A1 | 9/2016 | Czernik | |
| 2016/0278764 A1 | 9/2016 | Shelton, IV et al. | |
| 2016/0278765 A1 | 9/2016 | Shelton, IV et al. | |
| 2016/0278771 A1 | 9/2016 | Shelton, IV et al. | |
| 2016/0278774 A1 | 9/2016 | Shelton, IV et al. | |
| 2016/0278775 A1 | 9/2016 | Shelton, IV et al. | |
| 2016/0278777 A1 | 9/2016 | Shelton, IV et al. | |
| 2016/0278848 A1 | 9/2016 | Boudreaux et al. | |
| 2016/0287250 A1 | 10/2016 | Shelton, IV et al. | |
| 2016/0287251 A1 | 10/2016 | Shelton, IV et al. | |
| 2016/0296216 A1 | 10/2016 | Nicholas et al. | |
| 2016/0296226 A1 | 10/2016 | Kostrzewski | |
| 2016/0302791 A1 | 10/2016 | Schmitt | |
| 2016/0310134 A1 | 10/2016 | Contini et al. | |
| 2016/0324514 A1 | 11/2016 | Srinivas et al. | |
| 2016/0324518 A1 | 11/2016 | Nicholas et al. | |
| 2016/0338703 A1 | 11/2016 | Scirica et al. | |
| 2016/0345971 A1 | 12/2016 | Bucciaglia et al. | |
| 2016/0345973 A1 | 12/2016 | Marczyk et al. | |
| 2016/0354176 A1 | 12/2016 | Schmitt | |
| 2016/0374678 A1 | 12/2016 | Becerra et al. | |
| 2017/0000483 A1 | 1/2017 | Motai et al. | |
| 2017/0020525 A1 | 1/2017 | Shah | |
| 2017/0224339 A1* | 8/2017 | Huang | A61B 17/295 |
| 2017/0224343 A1* | 8/2017 | Baxter, III | A61B 17/00234 |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090251 A2 | 8/2009 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2777517 A1 | 9/2014 |
| EP | 2907456 A1 | 8/2015 |
| EP | 3120780 A2 | 1/2017 |
| EP | 3192455 A1 | 7/2017 |
| EP | 3398528 A1 | 11/2018 |
| FR | 391239 A | 10/1908 |
| FR | 2542188 A | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 20150191887 A1 | 12/2015 |

OTHER PUBLICATIONS

European Office Action dated May 6, 2021, issued in corresponding EP Appln. No. 20 166 542, 3 pages.

* cited by examiner

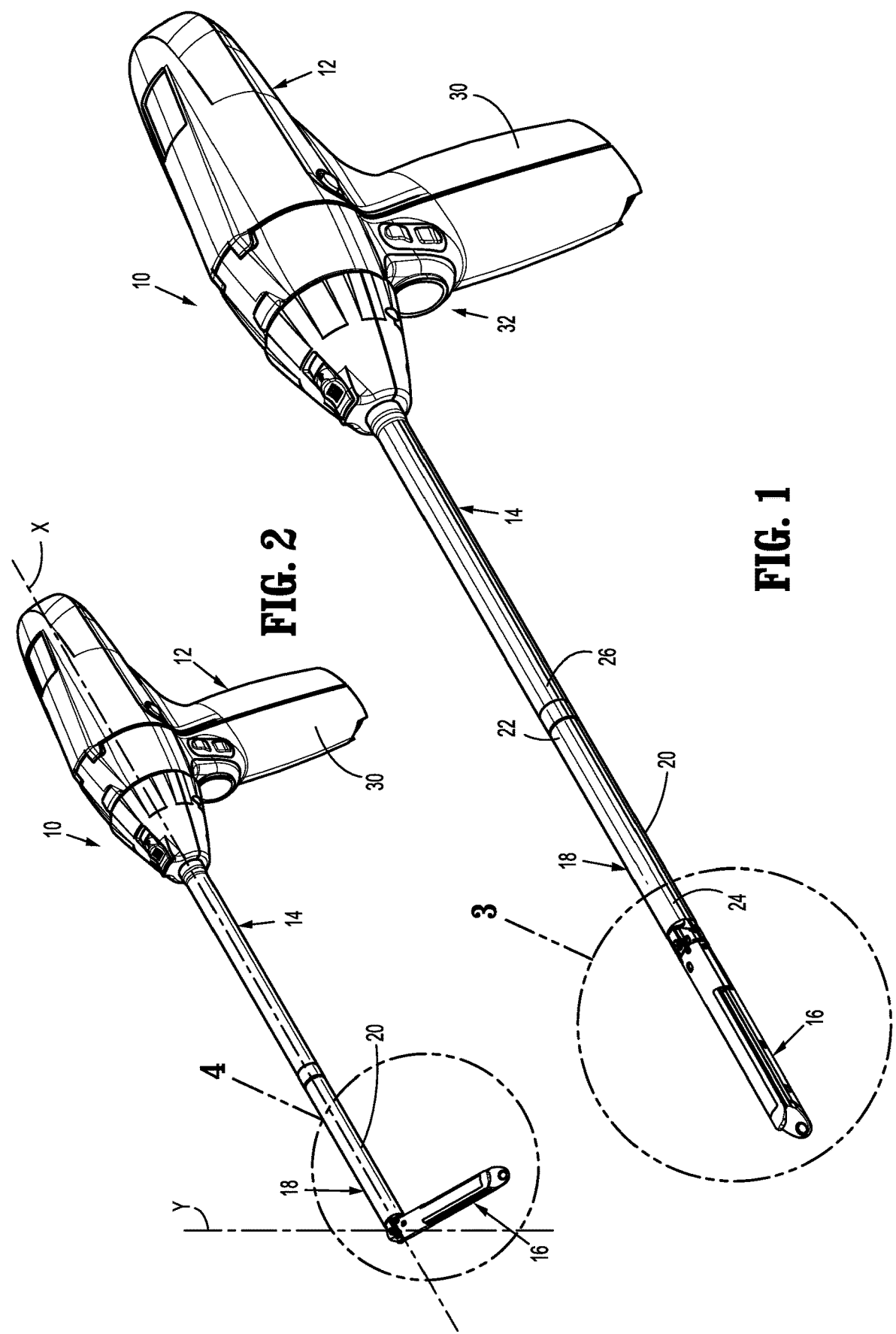

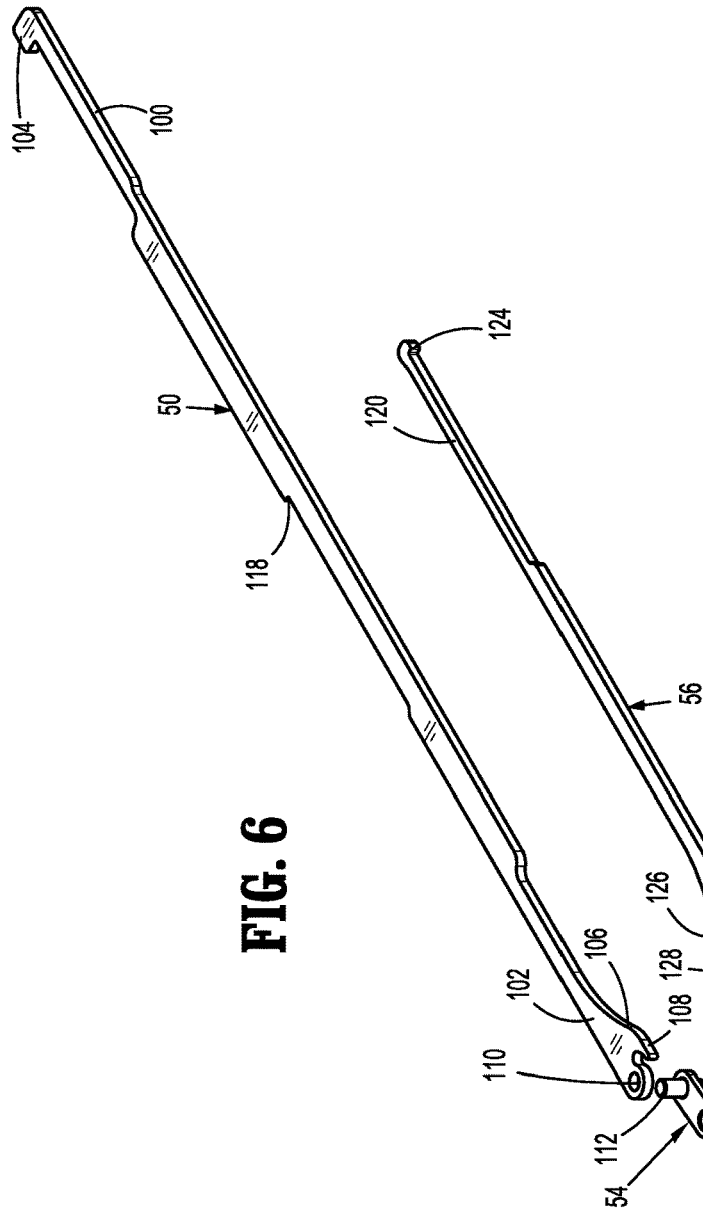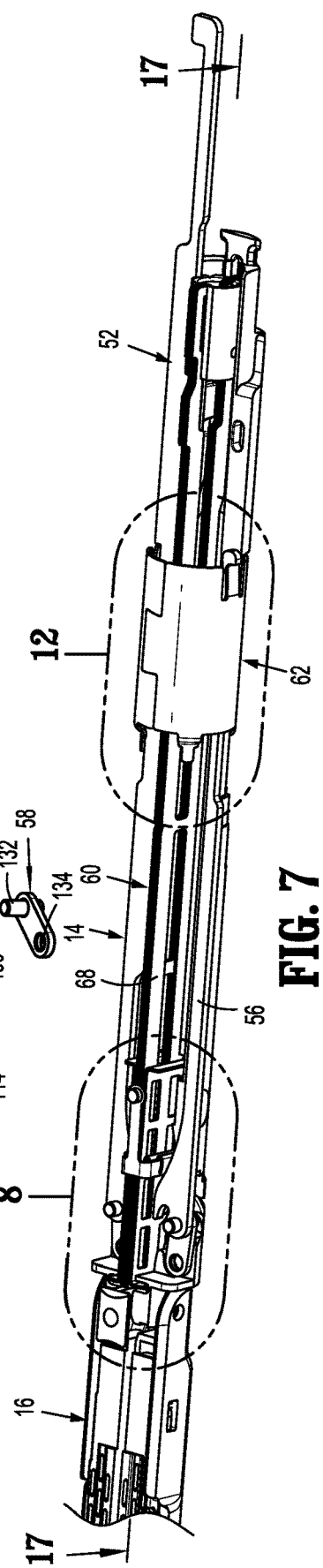
FIG. 6
FIG. 7

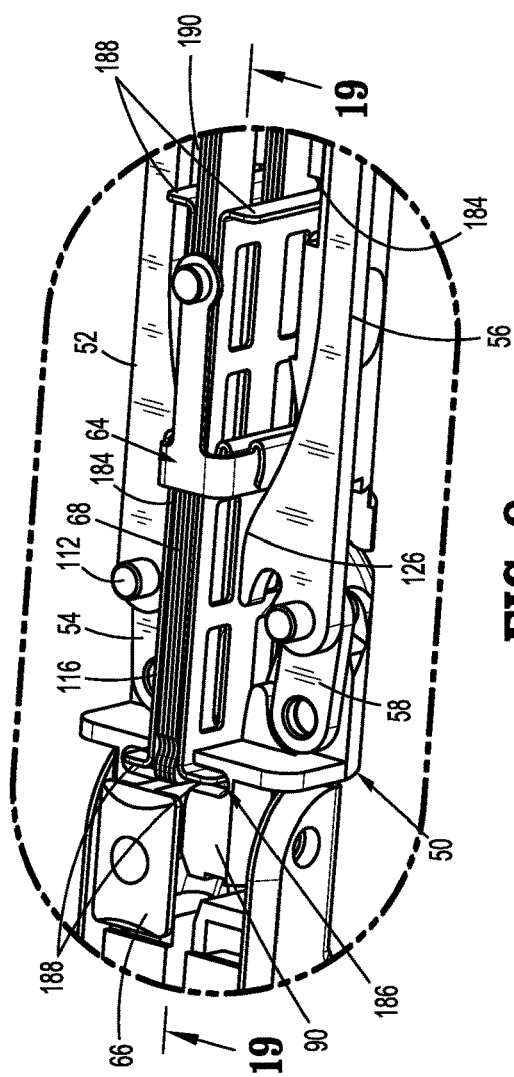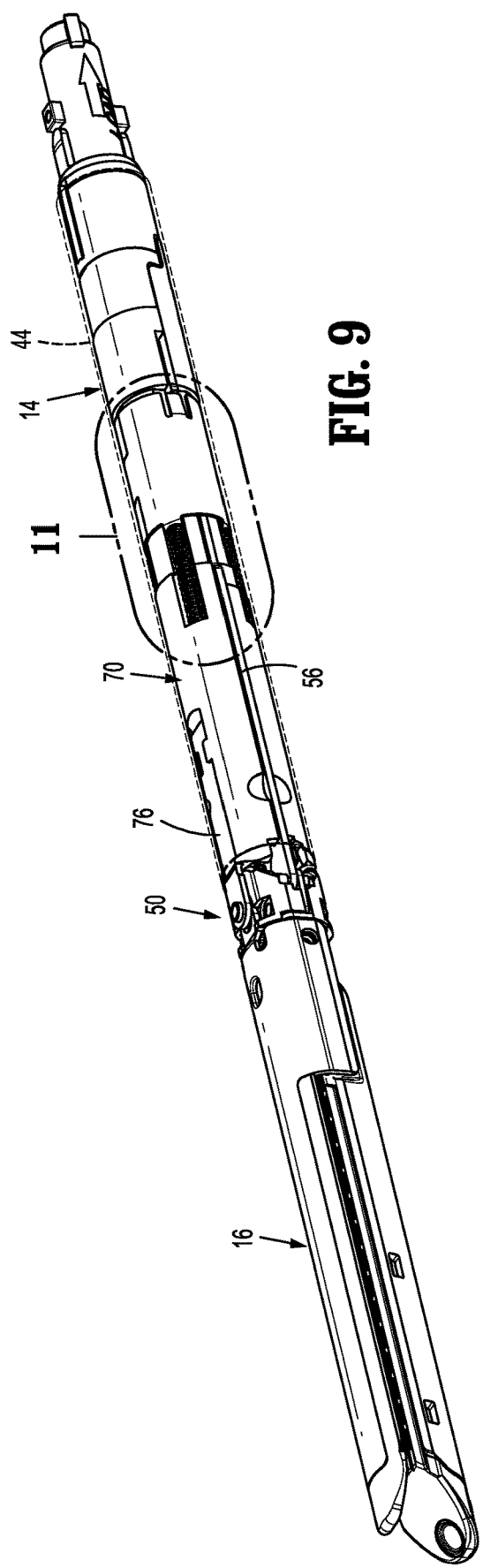

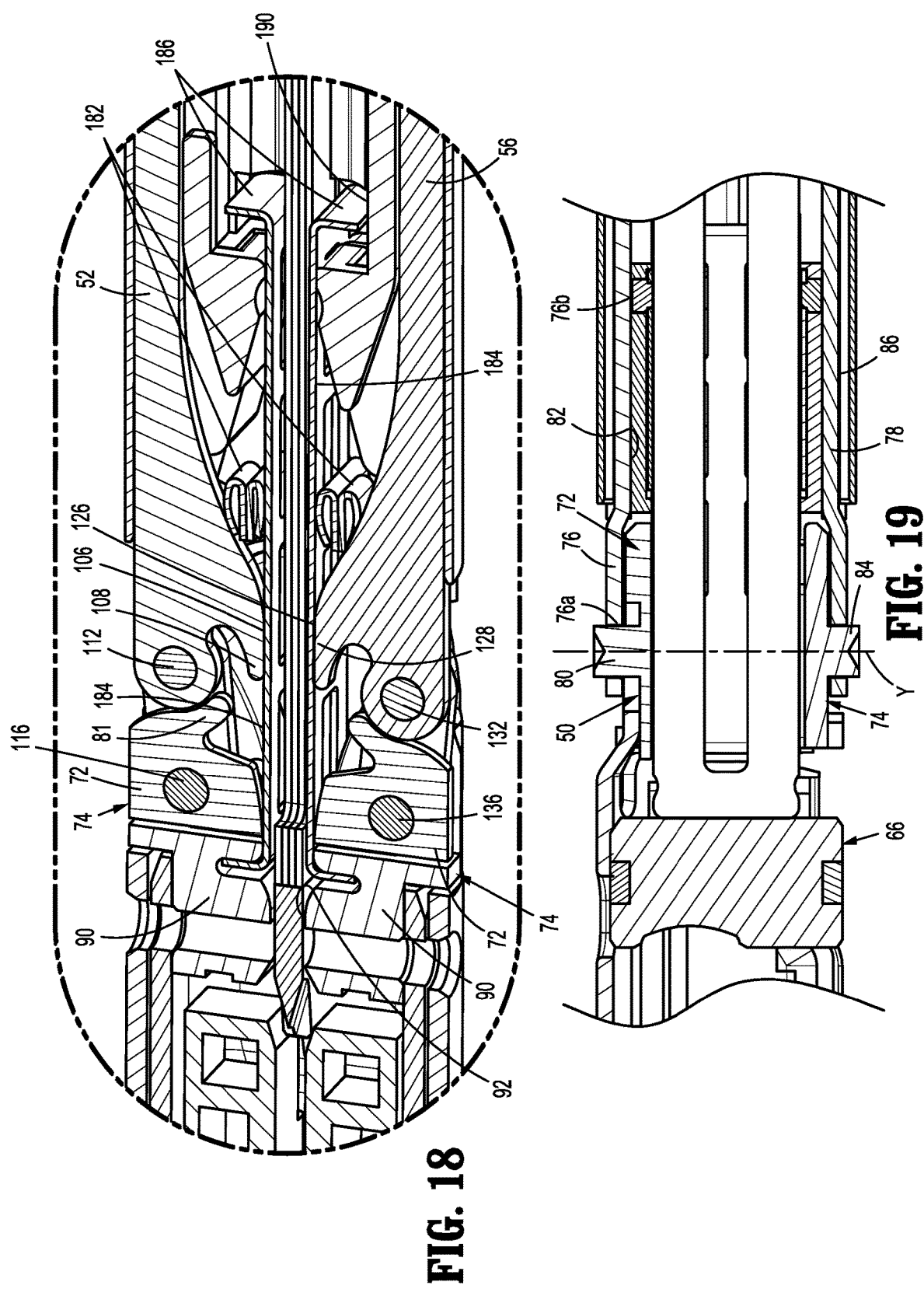

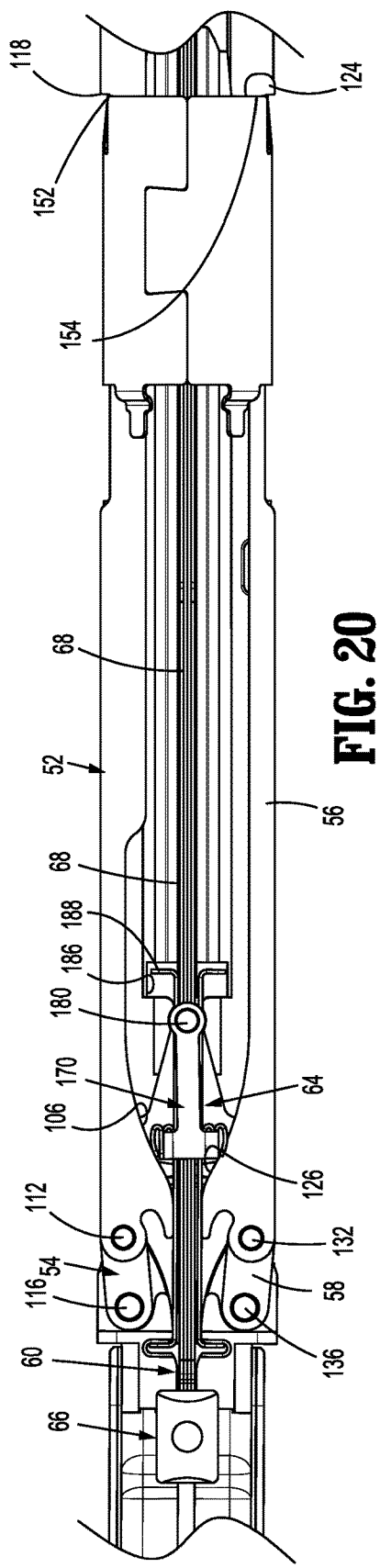
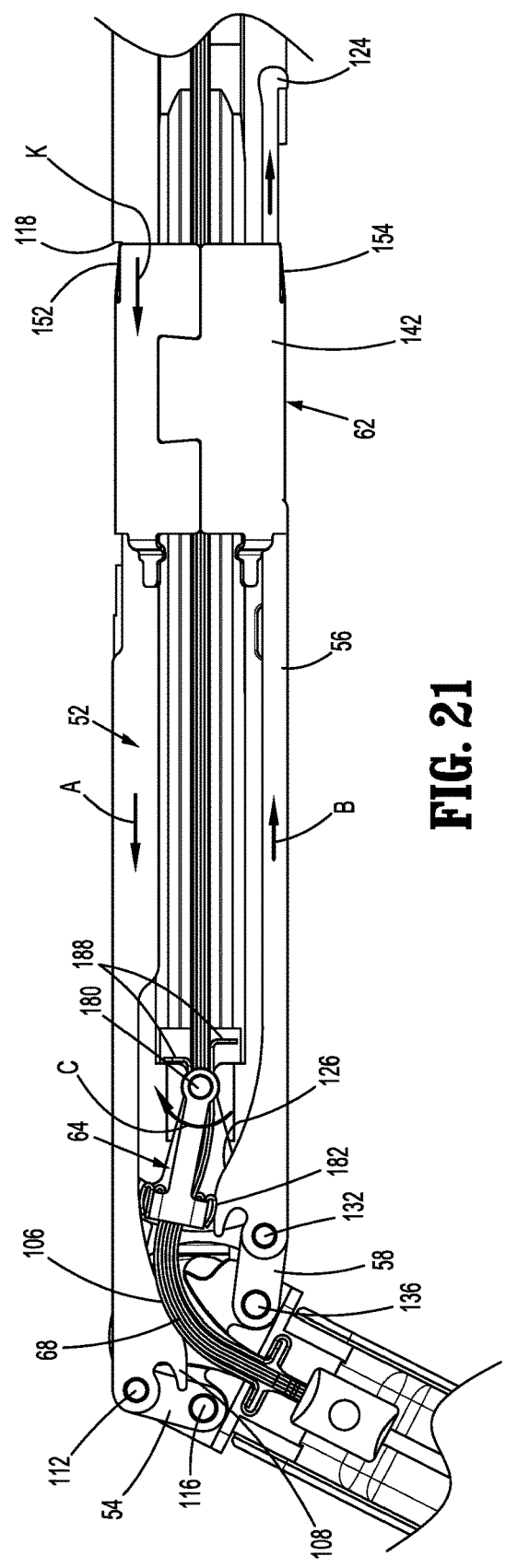

STAPLING DEVICE WITH ARTICULATING TOOL ASSEMBLY

CROSS-REFERENCE TO RELATED APPLICATIONS

This application claims the benefit of and priority to U.S. Provisional Patent Application Ser. No. 62/828,217 filed Apr. 2, 2019, the entire disclosure of which is incorporated by reference herein.

BACKGROUND

1. Technical Description

The present disclosure is directed to surgical stapling devices, and more particularly, to surgical stapling devices with tool assemblies that are supported on the stapling device for articulation.

2. Background of Related Art

Surgical stapling devices configured for endoscopic or laparoscopic use include an elongate body having a proximal portion and a distal portion, and a tool assembly supported on the distal portion of the elongate body. Typically, the tool assembly is supported by a pivot member that facilitates articulation of the tool assembly in relation to the elongate body. In some stapling devices, the tool assembly is limited to about 45 degrees of articulation about the pivot member in one or both directions.

Known stapling devices include an articulation mechanism that extends through a body of the stapling device and has a distal end that is coupled to the tool assembly. Typically, the articulation mechanism includes one or more articulation links that are movable along a longitudinal axis of the body of the stapling device to pivot the tool assembly about an axis transverse to the longitudinal axis.

In known stapling devices, the tool assembly is unstable when the tool assembly is in a non-articulated position, i.e., the position in which a longitudinal axis of the tool assembly is aligned with a longitudinal axis the elongate body. As such, the tool assembly becomes misaligned with the longitudinal axis of the body as the tool assembly is moved within a body cavity.

A continuing need exists in the art for a stapling device that includes a tool assembly that can be articulated over a wider range of angles and is stable in all positions of articulation including a non-articulated position.

SUMMARY

One aspect of the disclosure is directed to a surgical stapling device including a body portion, a mounting assembly, a drive assembly, an articulation assembly, and a gate assembly. The housing includes a proximal portion and a distal portion. The mounting assembly is pivotably supported on the distal portion of the housing about a pivot axis and movable between a non-articulated position and an articulated position. The drive assembly includes a flexible body having a working end. The drive assembly is movable within the housing from a retracted position to an advanced position. The articulation assembly includes an active articulation link having a proximal portion and a distal portion that is coupled to the mounting assembly. The active articulation link is movable between a retracted position and an advanced position to pivot the mounting assembly about the pivot axis. The gate assembly defines a channel that receives the flexible body of the drive assembly, wherein the active articulation link is positioned to engage the gate assembly when the active articulation link moves between its retracted and advanced positions to move the gate assembly to a position to increase the bending radius of the flexible body of the drive assembly.

In embodiments, the gate assembly is pivotably supported within the housing.

In some embodiments, the gate assembly includes an upper gate and a lower gate.

In certain embodiments, each of the upper and lower gates includes an elongate body and a U-shaped member supported on a distal portion, wherein the U-shaped members of the upper and lower gates define the channel.

In embodiments, the elongate body of each of the upper and lower gates includes a pivot member that pivotably connects the upper and lower gates within the housing.

In some embodiments, each of the U-shaped members of the upper and lower gates includes an engagement member, wherein the active articulation link is positioned to engage one of the engagement members of the upper or lower gates.

In certain embodiments, the articulation link includes a passive articulation link having a distal portion coupled to the mounting assembly such that pivotal movement of the mounting assembly about the pivot axis causes movement of the passive articulation link between retracted and advanced positions within the housing.

In embodiments, a blowout plate is supported on each side of the elongate body of the drive assembly. Each of the blowout plates includes a distal end supported on the mounting assembly at a position distally of the pivot axis and a proximal end supported within the housing proximally of the pivot axis.

In some embodiments, a stabilization mechanism is engaged with the active and passive articulation links and is configured to urge the mounting assembly to the non-articulated position.

In embodiments, a tool assembly is supported on the mounting assembly.

In some embodiments, the tool assembly includes a cartridge assembly and an anvil assembly.

In certain embodiments, the tool assembly is configured to receive the working end of the device assembly.

In embodiments, the distal portion of the active articulation link includes a hook and the mounting assembly includes a finger, wherein the hook is positioned to engage the finger when the active articulation link is moved towards the advanced position to assist in articulation of the mounting assembly.

In some embodiments, the active articulation link includes a first active articulation link and a second active articulation link that is pivotably coupled to the first active articulation link.

In certain embodiments, the distal portions of each of the active articulation link and the passive articulation link include a hook and the mounting assembly includes fingers, wherein the hooks are positioned to engage a respective one of the fingers when the respective active and passive articulation links are moved towards the advanced position to assist in articulation of the mounting assembly.

In embodiments, the active articulation link includes a first active articulation link and a second active articulation link that is pivotably coupled to the first active articulation link, and the passive articulation link includes a first passive articulation link and a second passive articulation link that is pivotably coupled to the first passive articulation link.

BRIEF DESCRIPTION OF THE DRAWINGS

Various embodiments of the presently disclosed surgical stapling device are described herein below with reference to the drawings, wherein:

FIG. 1 is a side perspective view of an exemplary embodiment of the presently disclosed surgical stapling device with a tool assembly of the stapling device in a non-articulated position;

FIG. 2 is a side perspective view of the surgical stapling device shown in FIG. 1 with the tool assembly of the stapling device in an articulated position;

FIG. 5A is a cross-sectional view taken along section line 5A-5A of FIG. 5;

FIG. 6 is a side perspective view of articulation links of an articulation assembly of the reload shown in FIG. 5;

FIG. 7 is a side perspective view of a proximal portion of the reload shown in FIG. 5 with an outer tube and the anvil assembly removed and the tool assembly in the non-articulated position;

FIG. 8 is an enlarged view of the indicated area of detail shown in FIG. 7;

FIG. 9 is a side perspective view of the reload shown in FIG. 5 assembled in the non-articulated position with the outer tube of the reload removed;

FIG. 18 is an enlarged view of the indicated area of detail shown in FIG. 17;

FIG. 19 is a cross-sectional view taken along section line 19-19 of FIG. 8;

FIG. 20 is a top view of the proximal portion of the reload shown in FIG. 6 with the outer tube and a housing half-section removed and the tool assembly in the non-articulated position;

FIG. 21 is a top view of the proximal portion of the reload shown in FIG. 6 with the outer tube and a housing half-section removed and the tool assembly in the articulated position;

DETAILED DESCRIPTION OF EMBODIMENTS

Figure 3:
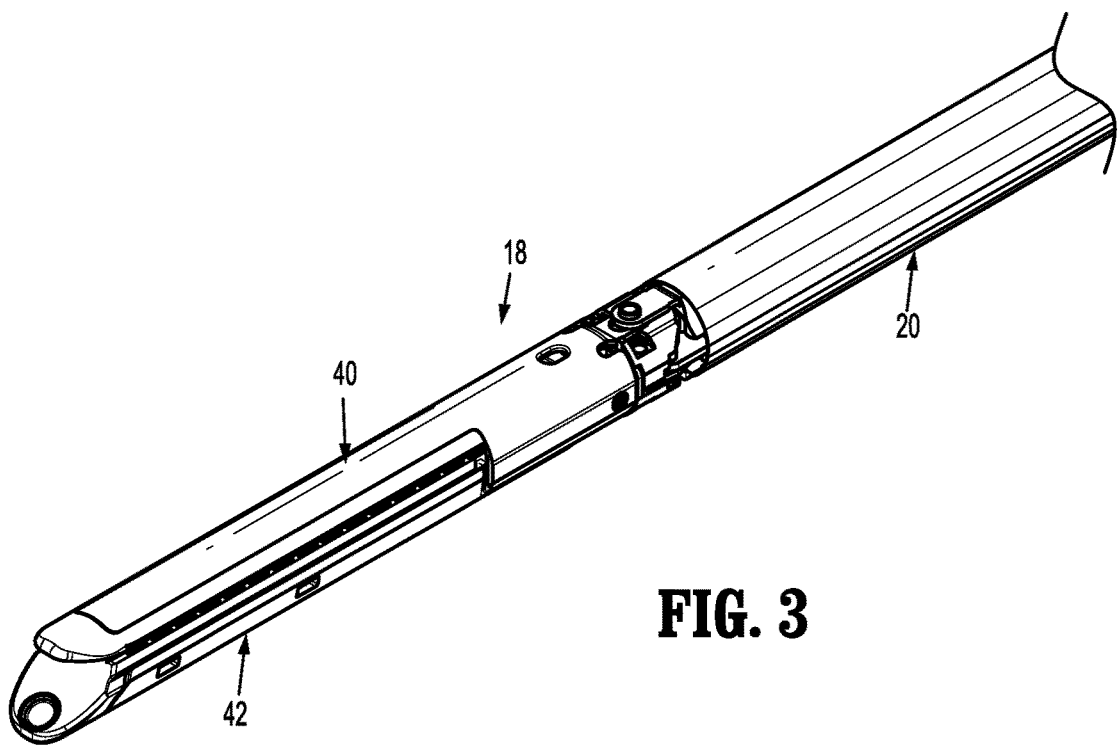
FIG. 3 is an enlarged view of the indicated area of detail shown in FIG. 1.

The presently disclosed device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Referring to FIGS. 1-4, the presently surgical stapling device is shown generally as stapling device 10 and includes a handle assembly 12, an adapter assembly 14, and a tool assembly 16. In embodiments, the tool assembly 16 forms part of a reload assembly 18 that includes the tool assembly 16 and a body portion 20 that has a proximal portion 22 and a distal portion 24. The adapter assembly 14 and the body portion 20 of the reload 18 define a longitudinal axis "X" (FIG. 2). The proximal portion 22 of the body portion 20 of the reload 18 is adapted to be coupled to a distal portion 26 of the adapter assembly 14 and the distal portion of the body portion 20 is pivotally coupled to the tool assembly 16 about a pivot axis "Y" (FIG. 2) that is substantially perpendicular to the longitudinal axis "X". The tool assembly 16 is pivotal between a non-articulated position (FIG. 1) in which the tool assembly 16 is aligned with the longitudinal axis "X" and articulated positions in which the tool assembly 16 defines an acute angle with the longitudinal axis "X". It is envisioned that the tool assembly 16 may be connected directly to the distal portion 26 of the adapter assembly 14 and need not form part of a reload assembly 18.

In embodiments, the handle assembly 12 is powered and includes a stationary handle 30 and actuation buttons 32 that can be actuated to control various functions of the stapling device 10 including approximation and firing of the tool assembly 16. U.S. Pat. No. 9,055,943 ("the '943 Patent") discloses a surgical stapling device having a powered handle assembly, an adapter assembly, and a tool assembly that is releasably coupled to the adapter assembly. The '943 Patent is incorporated herein by reference in its entirety. Alternately, the handle assembly 12 can be manually actuated such as described in U.S. Pat. No. 5,865,361 ("the '361 Patent") which is incorporated herein by reference in its entirety.

Figure 4:
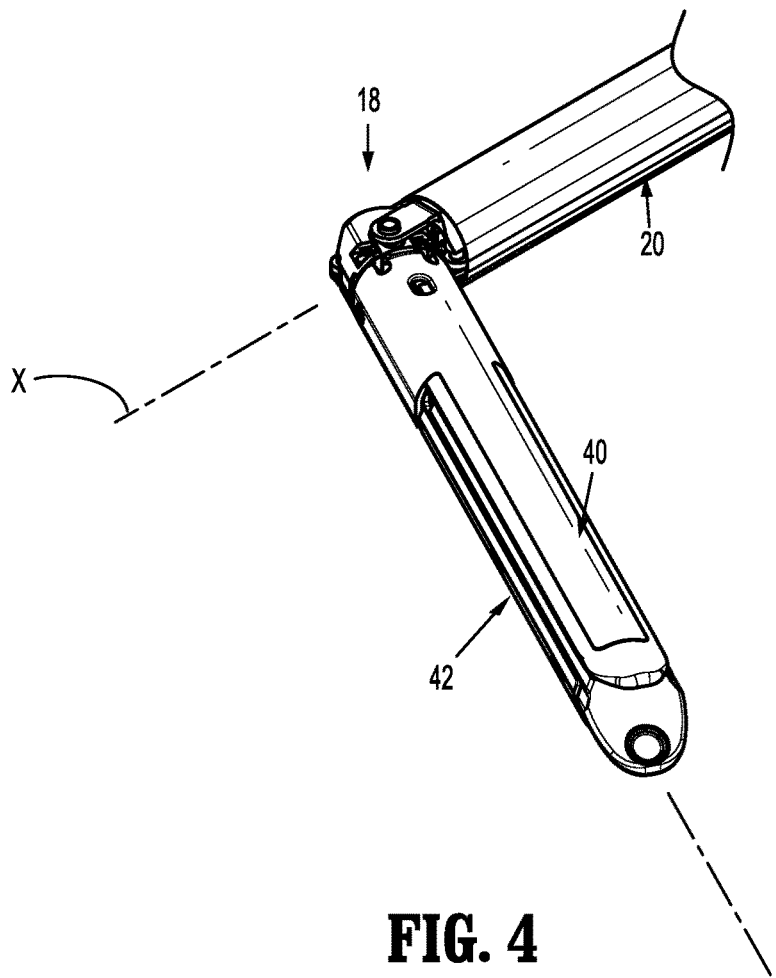
FIG. 4 is an enlarged view of the indicated area of detail shown in FIG. 2.
Figure 5:
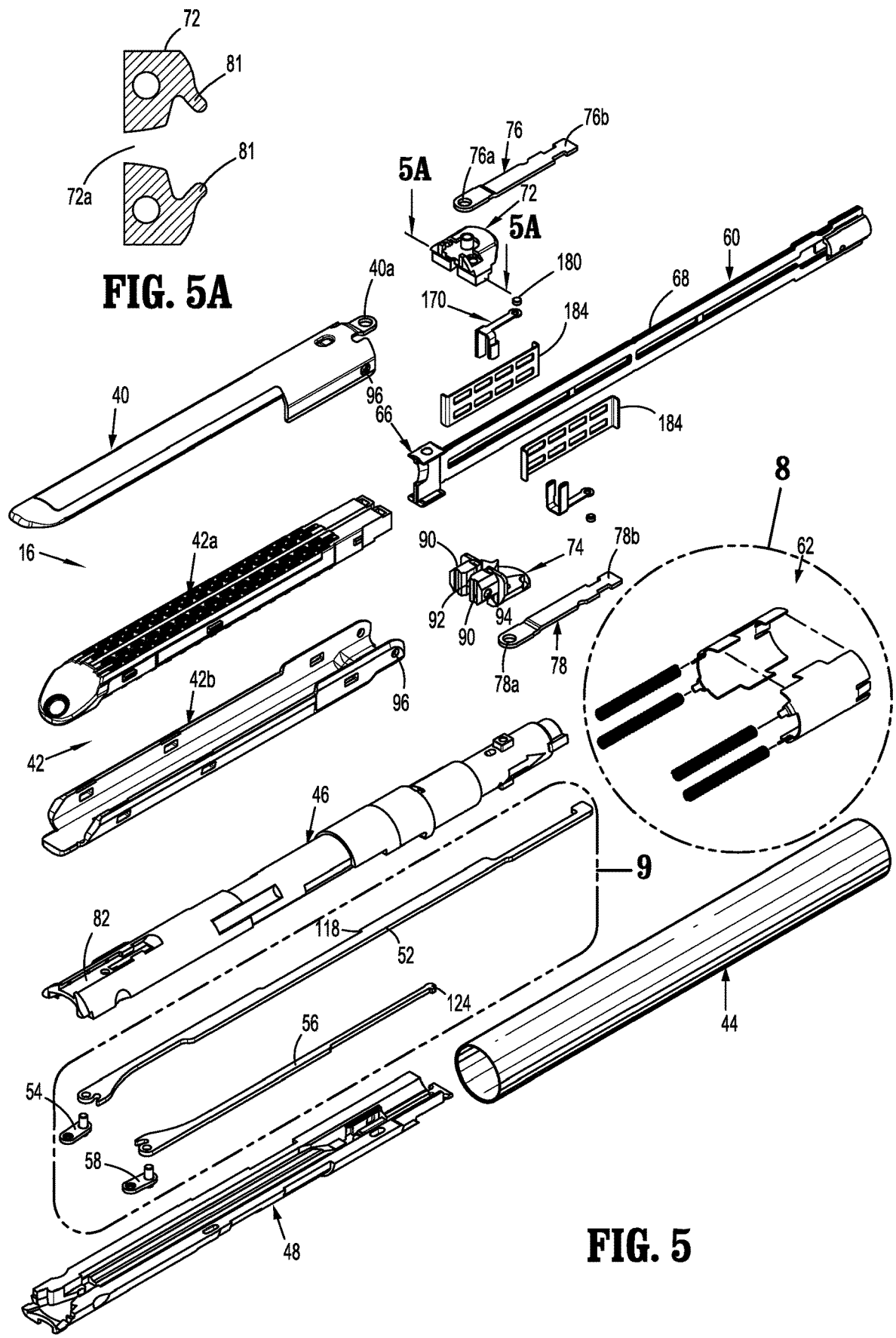
FIG. 5 is a side perspective exploded view of a reload of the stapling device shown in FIG. 1 including the tool assembly.
Figure 10:
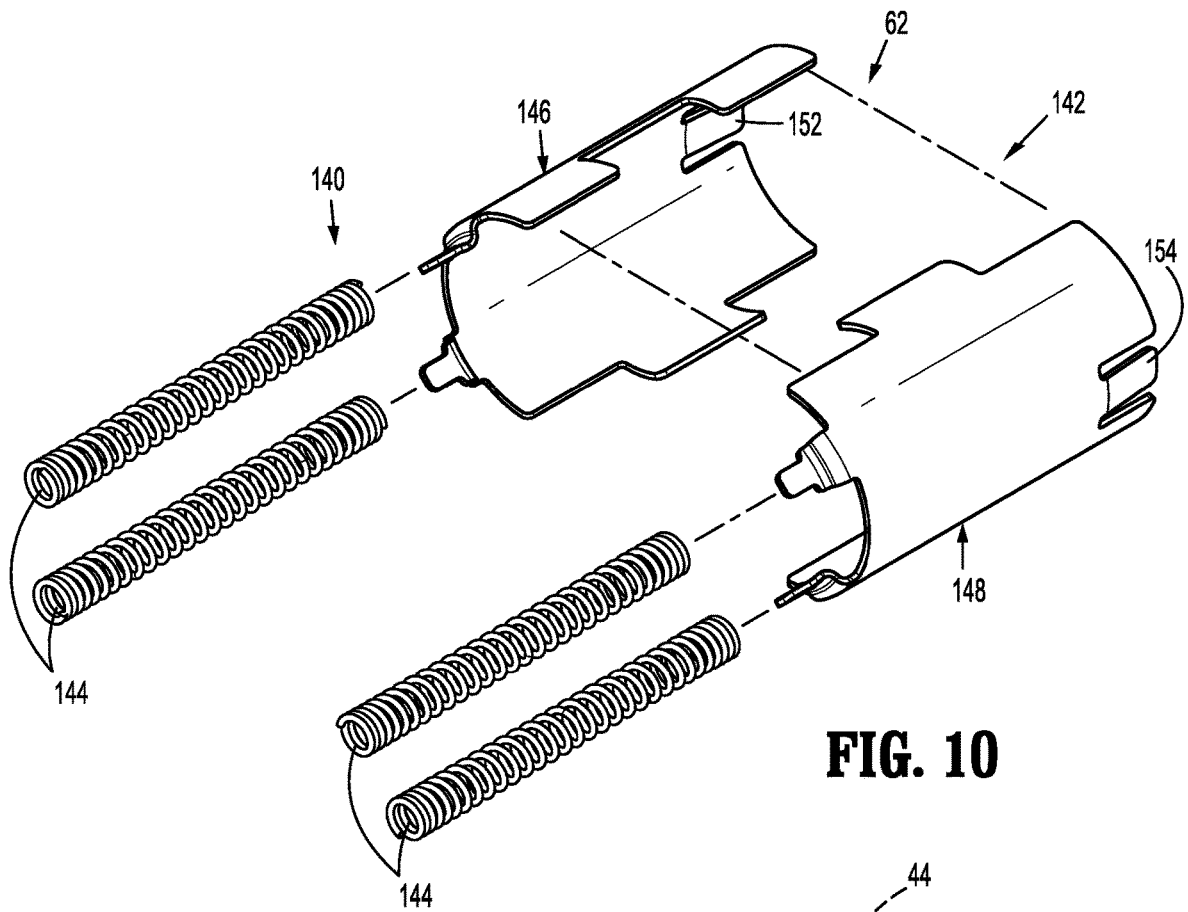
FIG. 10 is a side perspective view of a stabilization system of the reload assembly shown in FIG. 5.
Figure 11:
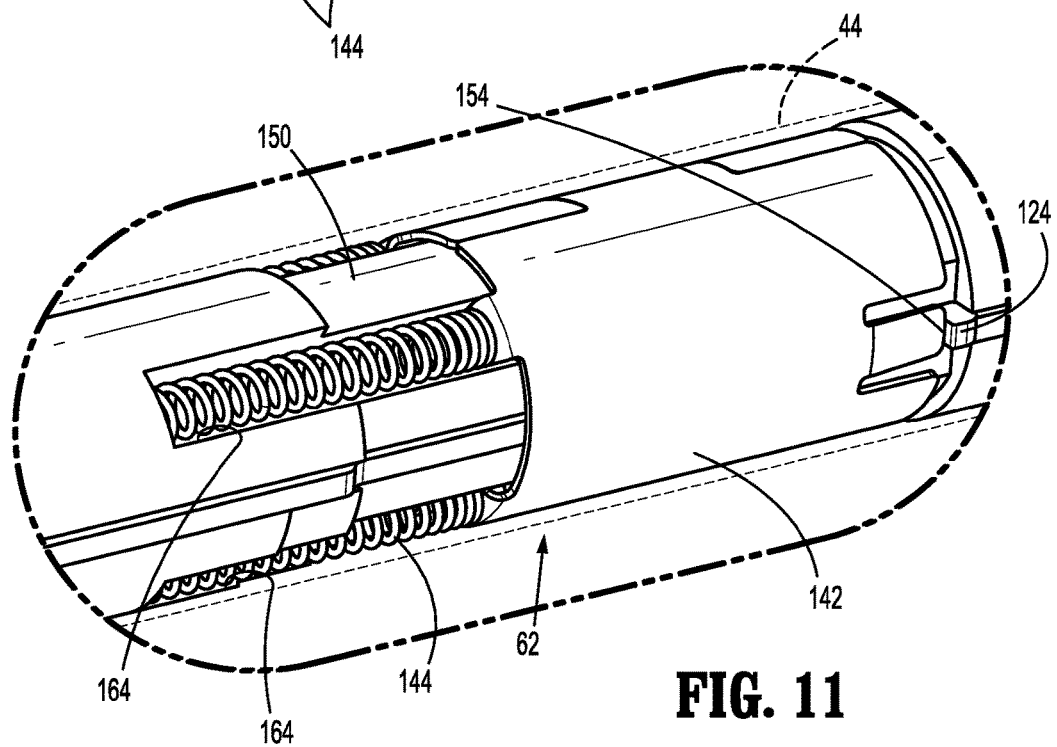
FIG. 11 is an enlarged view of the indicated area of detail shown in FIG. 9.
Figure 12:
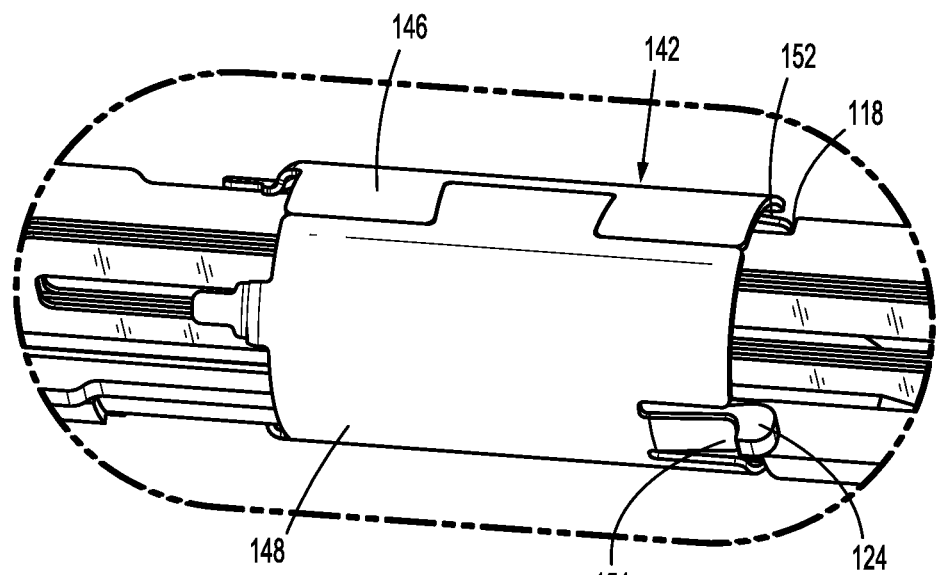
FIG. 12 is an enlarged view of the indicated area of detail shown in FIG. 7.
Figure 13:
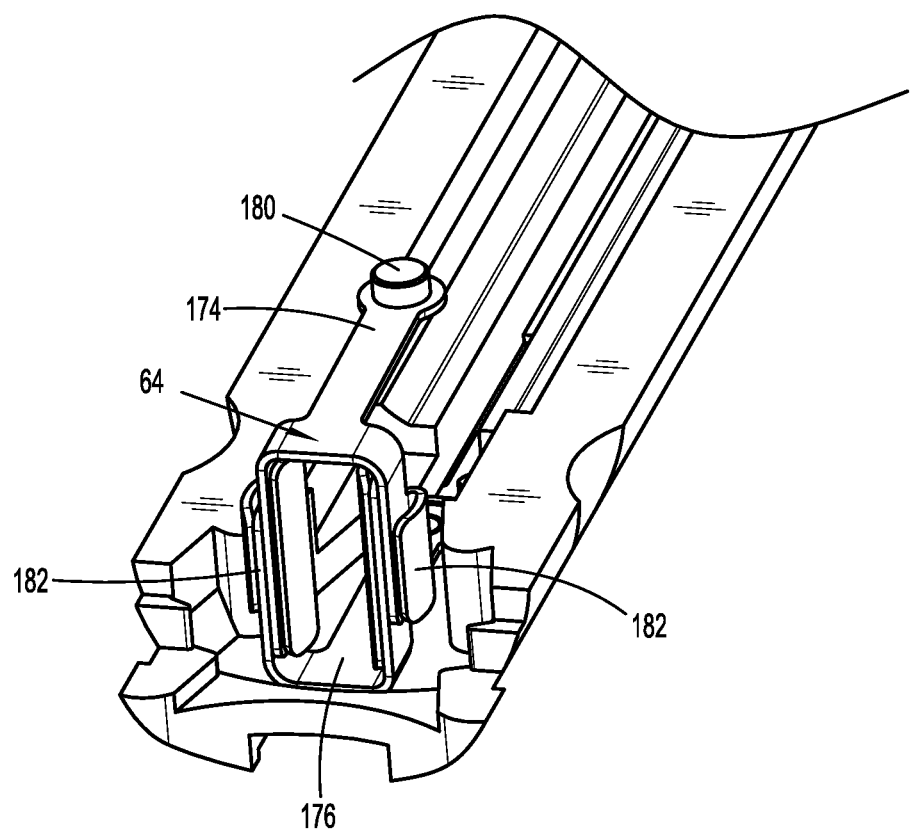
FIG. 13 is a perspective view from the distal end of a distal portion of a housing half-section of a proximal body portion of the reload shown in FIG. 5 with a gate assembly supported in the housing half-section.
Figure 16:
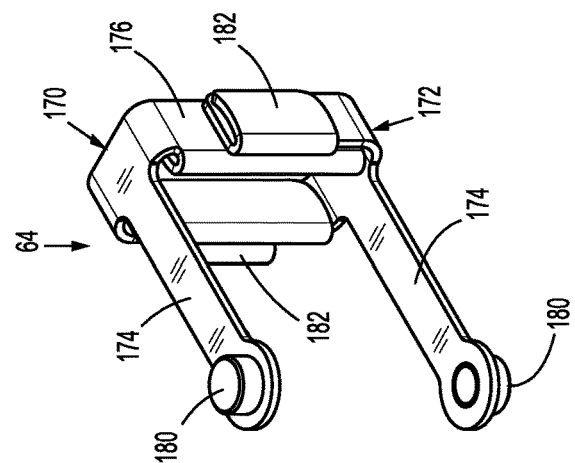
FIG. 16 is a side perspective view from the proximal end of the gate assembly of the reload shown in FIG. 5.
Figure 15:
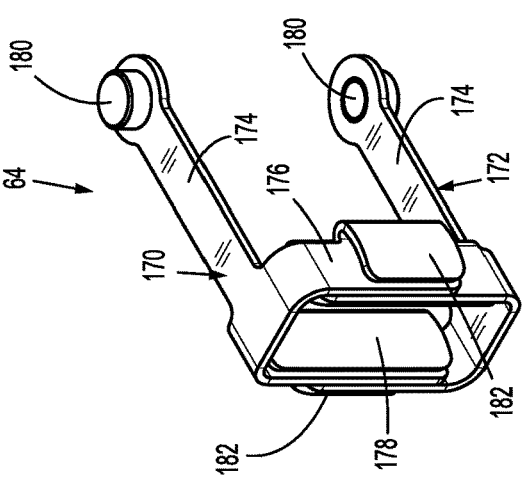
FIG. 15 is a side perspective view from the distal end of the gate assembly of the reload shown in FIG. 5.
Figure 14:
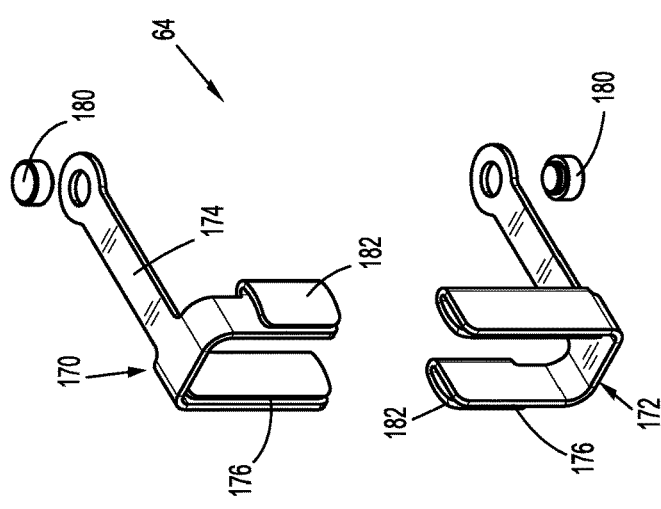
FIG. 14 is an exploded side perspective view of the gate assembly of the reload shown in FIG. 5.
Figure 17:
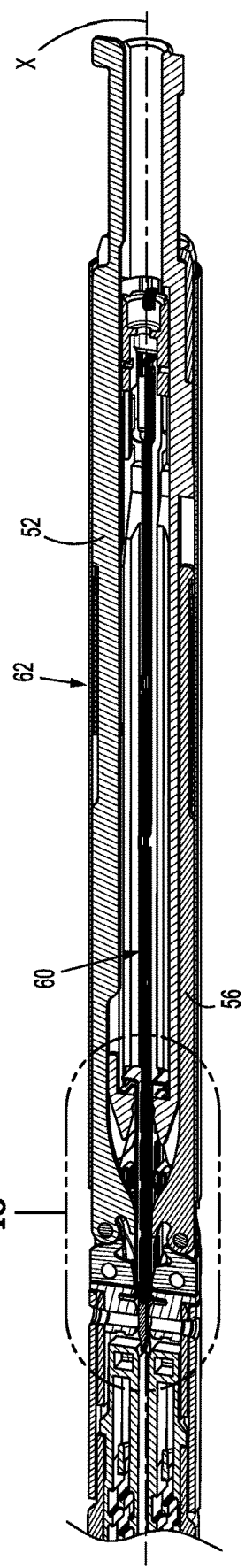
FIG. 17 is a cross-sectional view taken along section line 17-17 of FIG. 7.

Referring to FIGS. 3-5, the tool assembly 16 includes an anvil assembly 40 and a cartridge assembly 42. In embodiments, the cartridge assembly 42 includes a staple cartridge 42a and channel 42b and is pivotally coupled to the anvil assembly 40 between an open position and a clamped position. Alternatively, it is envisioned that the cartridge assembly 42 can be stationary and the anvil assembly 40 can be movable between the open and clamped positions such as described in the '361 Patent.

Referring to FIG. 5, the body portion 20 of the reload assembly 18 (FIG. 1) includes an outer casing 44, a first housing half-section 46, a second housing half-section 48, a mounting assembly 50, first and second active articulation links 52, 54, first and second passive articulation links 56, 58, a drive assembly 60, an articulation stabilization mechanism 62, and a gate assembly 64. The drive assembly 60 of the reload assembly 18 includes a flexible body 68 having a working end 66. The working end 66 is movable through the tool assembly 16 to actuate the tool assembly 16 as is known in the art. For a more detailed description of the structure and operation of the drive assembly 60, see the '361 Patent. The first and second housing half-sections 46, 48, respectively, are secured together to define a housing 70 that supports the articulation links and the articulation stabilization mechanism 62 as described in further detail below.

The mounting assembly 50 (FIG. 19) includes a first mounting portion 72, a second mounting portion 74, a first coupling member 76, and a second coupling member 78. The first mounting portion 72 defines a longitudinal slot 72a and includes a pivot member 80 and internal fingers 81. The internal fingers 81 are positioned to engage the articulation links 52 and 56 during articulation of the tool assembly 16 as discussed in further detail below. The first coupling member 76 has a first end that defines an opening 76a that receives the pivot member 80 and a second end 76b that is received within a recess 82 defined in a distal end of the first housing half-section 46 of the reload 18 such that the first coupling member 76 pivotably secures the tool assembly 16 to the first housing half-section 46. The pivot member 80 is also received in an opening 40a (FIG. 5) defined in a proximal end of the anvil assembly 40 to pivotally couple the anvil assembly 40 to the first mounting portion 72 of the mounting assembly 50.

The second mounting portion 74 also includes a pivot member 84 (FIG. 19). The second coupling member 48 has a first end defining an opening 74a that receives the pivot member 84 of the second mounting portion 74 and a second end that is received within a recess 86 defined within the second housing half-section 48 to pivotally secure the second mounting portion 74 to the second housing half-section 48 of the body portion 20 of the reload assembly 18. The outer casing 44 of the proximal portion 22 of the reload 18 is positioned about the first and second housing half-sections 46, 48 to prevent separation of the first and second housing half-sections 46, 48 from one another and to prevent the second ends of the first and second coupling members 76, 78 from moving from within the recesses 82, 86, respectively.

The second mounting portion 74 includes distal extensions 90 that define a slot 92 that is aligned with the slot 72a in the first mounting portion 72. The distal extensions 90 are received in a proximal end of the anvil assembly 40 (FIG. 18) and define openings 94. The proximal ends of the anvil assembly 40 and the channel 42b of the cartridge assembly 42 also define openings 96 that are aligned with the openings 94 in the second mounting portion 74 of the mounting assembly 50. The openings 94 and 96 receive pivot members (not shown) to secure the anvil assembly 40 to the second mounting portion 74 and to pivotably secure the cartridge assembly 42 to the anvil assembly 40 about the pivot axis "Y" (FIG. 19).

Referring to FIGS. 3-5, the first and second mounting portions 72, 74, respectively, are secured together using pins or rivets to fixedly secure the tool assembly 16 to the mounting assembly 50. For a more detailed description of the interconnection between the mounting assembly 50 and the tool assembly 16, see the '361 Patent.

Referring to FIGS. 5-8, the first and second active articulation links 52, 54, respectively, are supported between the first and second housing half-sections 46, 48 on opposite sides of the housing 70 of the body portion 20. The first active articulation link 52 is elongate and includes a proximal portion 100 and a distal portion 102. The proximal portion 100 is adapted to engage an articulation drive mechanism (not shown) located within the adapter assembly 14 to translate motion of the drive mechanism into longitudinal movement of the articulation link 52. In embodiments, the proximal portion 100 may include a transverse extension 104 that is positioned to engage the articulation drive mechanism (not shown) of the adapter assembly 14 as known in the art. Alternately, it is envisioned that the active articulation link 52 can engage the drive mechanism (not shown) of the adapter assembly 14 using a variety of different configurations or coupling devices. The distal portion 102 of the articulation link 52 includes an inner cam surface 106, a hook 108, and an opening 110. The cam surface 106 forms the inner surface of the hook 108 and is positioned to support one side of the drive assembly 60 as described in further detail below. The cam surface 106 defines a curved surface that extends towards the longitudinal axis "X" in a distal direction.

The function of the hook 108 will be described in further detail below. The opening 110 receives a pivot member 112 that is supported on the second active articulation link 54 to pivotally couple the second active articulation link 54 to the distal portion 102 of the first active articulation link 52.

The second active articulation link 54 also includes a distal portion that defines an opening 114. The opening 114 receives a pivot member 116 (FIG. 18) that is supported on a first side of the mounting assembly 50 at a position transversely offset from the pivot axis "Y" (FIG. 2) to pivotally secure the second active articulation link 54 to the mounting assembly 50. Although not shown, the first active articulation link 52 is confined to linear movement within the housing 50 of the body portion 20 of the reload assembly 18. Pivotally coupling the second articulation link 54 between the first articulation link 52 and the mounting assembly 50 increases the range of articulation of the tool assembly 16 in relation to the adapter assembly 14 that is possible. When the first active articulation link 52 is moved longitudinally within the body portion 20 of the reload 18, the second active articulation link 54 is advanced and pivoted about the pivot member 112 to cause pivotal movement of the tool assembly 116 about the axis "Y" (FIG. 2). It is noted that the length of the second active articulation link 54 is substantially shorter than the length of the first active articulation link 52 such that the links 52 and 54 do not protrude outwardly of the mounting assembly 50 beyond a predetermined distance when the mounting assembly 50 and tool assembly 16 are articulated.

The first active articulation link 52 also defines a bushing engagement surface 118. In embodiments, the bushing engagement surface 118 is positioned between the proximal and distal portions 100, 102 and is positioned to interact with the stabilization mechanism 62 (FIG. 5) to provide stability to the tool assembly 16 in the non-articulated position of the tool assembly as described in detail below.

The first passive articulation link 56 includes an elongate body having a proximal portion 120 and a distal portion 122. The proximal portion 120 includes a bushing engagement surface 124 that is positioned to interact with the stabilization mechanism 62 (FIG. 5) to provide stability to the tool assembly 16 in the non-articulated position of the tool assembly 16 as described in detail below. The distal portion 122 of the articulation link 56 includes an inner cam surface 126, a hook 128, and an opening 130. The cam surface 126 forms the inner surface of the hook 128 and is positioned to engage one side of the drive assembly 60 as described in further detail below. The cam surface 126 defines a curved surface that extends towards the longitudinal axis "X" in a distal direction. The function of the hook 128 will be described in further detail below. The opening 130 receives a pivot member 132 that is supported on the second passive articulation link 58 to pivotally couple the second passive articulation link 58 to the distal portion 122 of the first passive articulation link 52.

The second passive articulation link 58 also includes a distal portion that defines an opening 134. The opening 134 receives a pivot member 136 that is supported on a second side of the mounting assembly 50 to pivotally secure the second passive articulation link 58 to the mounting assembly 50 at a position transversely offset from the pivot axis "Y" (FIG. 2). Although not shown, the first passive articulation link 56 is confined to linear movement within the housing 50 of the body portion 20 of the reload assembly 18. As described above in regard to second active articulation link 54, pivotally coupling the second passive articulation link 58 between the first passive articulation link 56 and the mounting assembly 50 increases the range of articulation of the tool assembly 16 in relation to the adapter assembly 14. As discussed above in regard to the second active articulation link 54, the length of the second passive link 58 is substantially shorter than the length of the first passive articulation link 56 such that the links 56 and 58 do not protrude outwardly of the mounting assembly 50 beyond a predetermined distance.

Referring also to FIGS. 9-12, the articulation stabilization system 62 includes a biasing mechanism 140 including a slide member 142 and a plurality of springs 144. In embodiments, the slide member 142 is substantially annular and includes a first half-section 146 and a second half-section 148. The slide member 142 is slidably positioned within a recess 150 defined in an outer surface of the housing 70 of the body portion 20 of the reload assembly 18. The slide member 142 includes distally extending spring mounting tabs 150, a first proximally extending bushing 152, and a second proximally extending bushing 154. In embodiments, each of the half-sections 146, 148 of the slide member 142 includes respective side wall recesses 160 and side wall extensions 162 that mesh to form the annular slide member 142.

In embodiments, the springs 144 are coil springs that have a proximal portion that is received about the spring mounting tabs 150 of the slide member 142. Each of the springs 144 is positioned within a respective pocket 164 defined in the housing 22 to urge the slide member 142 distally about the housing 22. The first bushing 152 of the slide member 142 is received within the notch 118 of the first active articulation link 52 to urge the articulation link 52 proximally to a position in which the tool assembly 16 is in the non-articulated position. When the articulation link 52 is positioned such that the tool assembly 16 is in the non-articulated position, the springs 144 are in an unbiased state with the bushing 152 positioned within the notch 118 and engaged with the articulation link 52. In addition, bushing 154 is positioned within the surface 124 in engagement with the first passive articulation link 56 to urge the articulation link 56 proximally to a position in which the tool assembly 16 is also in the non-articulated position. When the articulation link 56 is positioned such that the tool assembly 16 is in the non-articulated position, the springs 144 are in an unbiased state with the bushing 154 engaged positioned within the surface 124 of the articulation link 56.

For a more detailed description of the presently disclosed stabilization system 62, see U.S. Patent Application No. 62/585,703 ("the '703 Application") which was filed on Nov. 14, 2017 and is incorporated herein by reference in its entirety.

Referring also to FIGS. 13-16, the gate assembly 64 includes an upper gate 170 and a lower gate 172. Each of the upper and lower gates 170, 172, respectively, includes an elongate body 174 and a U-shaped member 176. When the upper and lower gates 170, 172 are assembled, the gates 170, 172 define a channel 178. The channel 178 is dimensioned to receive and allow passage of the flexible body 68 of the drive assembly 60 as the drive assembly 60 is moved between retracted and advanced positions to approximate and fire staples from the stapling device 10 as is known in the art.

The elongate body 174 of each of the gates 170, 172 includes a pivot member 180 that is pivotally coupled to an inner wall of the housing 70 of the body portion 20 of the reload assembly 18 to axially fix the gates 170, 172 within the housing 70 while permitting pivotal movement of the gates 170, 172 within the housing 70. Each of the U-shaped members 176 of the gates 170, 172 may have an engagement member 182 that is positioned to abut the cam surfaces 106, 126 of the articulation links 52, 56, respectively, as described in further detail below. In use, the gates 170, 172 increase a bending radius of the flexible body 68 of the drive assembly 60 when the tool assembly 16 is in an articulated position in relation to the adapter assembly 14.

Referring again to FIGS. 5 and 8, the reload assembly 18 also includes blow out plates 184. The blowout plates 184 are positioned on opposite sides of the flexible body 68 of the drive assembly 60 and extend from a position distal of the pivot axis "Y" (FIG. 2) to a position proximal of the pivot axis "Y". In embodiments, distal ends of the blow out plates 184 are secured within a slot 186 (FIG. 8) in the mounting assembly 50. In some embodiments, a proximal end of the blowout plates 184 includes a transverse portion 188 that is received within a recess 190 (FIG. 8) within the housing 70 of the body portion 20 to allow the proximal end of the blow out plates 184 to slide within the housing 70. The sliding movement allows the blowout plates 184 to adjust accordingly when the radius of curvature changes as the tool assembly 16 is articulated about the pivot axis "Y". The blowout plates 184 are positioned to obstruct outward bulging of the flexible body 68 of the drive assembly 60 during approximation and firing of the stapling device 10. See the '361 patent for a more detailed description of the blowout plates 184.

Referring to FIGS. 17-20, when the tool assembly 18 of the reload 18 is in a non-articulated position, the flexible body 68 of the drive assembly 60 extends along the longitudinal axis "X" of the body portion 20 of the reload 18 between the blowout plates 184 and through the channel 178 of the gate assembly 64. In addition, the articulation links 52 and 56 are urged to neutral positions by the stabilization mechanism 62. In their neutral positions, the cam surface 106, 128 of the articulation links 52, 56 are positioned in engagement with outer walls of the blowout plates 184 and the gates assembly 64 is positioned such that the channel 178 defines by the gate assembly 64 is aligned with the longitudinal axis "X". It is noted that the engagement members 182 of the gates 170, 172 of the gate assembly 64 are positioned towards a proximal end of the cam surfaces 106, 126. As discussed above, the cam surfaces 106, 126 define curved surfaces that extend towards the longitudinal axis "X" in a distal direction.

Figure 22:
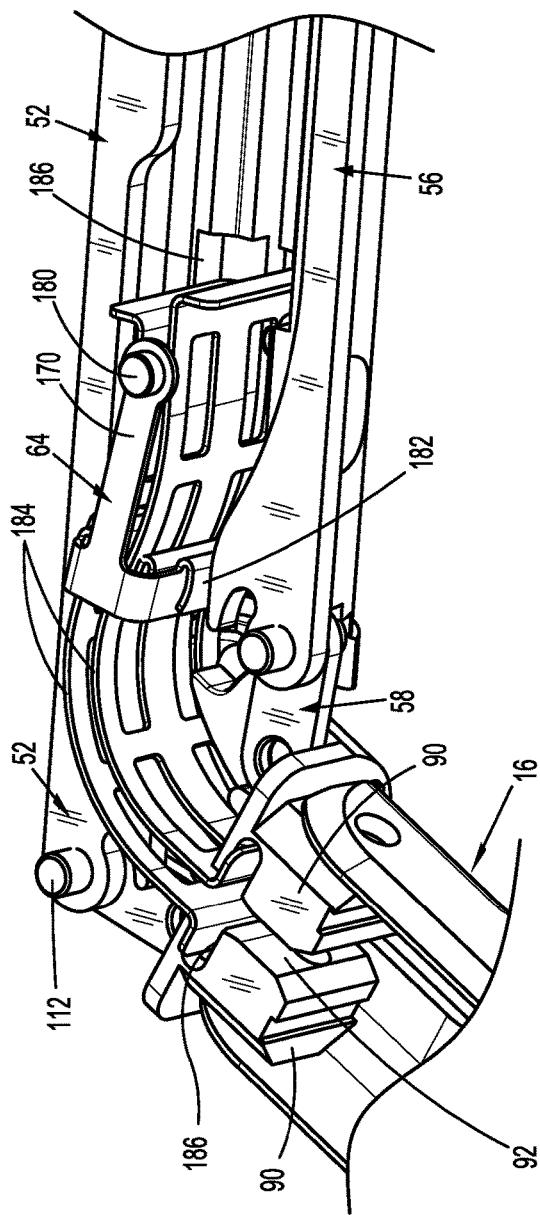
FIG. 22 is a side perspective view of the proximal end of the tool assembly and the distal end of the proximal body portion with the drive assembly removed and the tool assembly in an articulated position.
Figure 23:
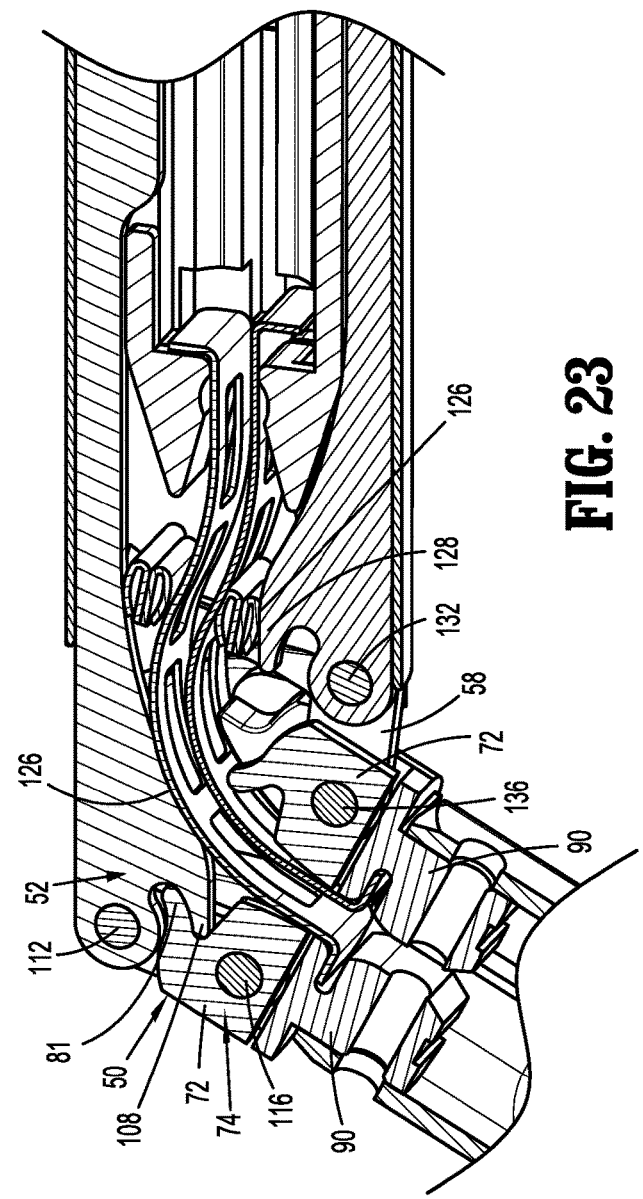
FIG. 23 is a cross-sectional view through the proximal end of the tool assembly and the distal end of the proximal body portion with the drive assembly removed and the tool assembly in an articulated position.

Referring to FIGS. 21-23, when the active articulation link 52 is advanced in the direction indicated by arrows "A" in FIG. 21 by actuating the drive mechanism in the adapter assembly 14 (FIG. 1), the first active articulation link 52 advances the second active articulation link 54 to pivot the mounting assembly 50 and the tool assembly 16 about the pivot axis "Y" (FIG. 19). As the tool assembly 16 pivots about the pivot axis "Y", the second passive articulation link 58 is moved proximally by the pivot member 136 of the mounting assembly 50. As the second passive articulation link 58 is moved proximally, the first passive articulation link 56 which is pivotally coupled to the second passive articulation link 58 also moves proximally in the direction indicated by arrow "B" in FIG. 21.

When the tool assembly 16 is pivoted about the pivot axis "Y", the flexible body 68 of the drive assembly 60 bends about the pivot axis "Y" (FIG. 19). As discussed above, the gates 170, 172 (FIG. 14) of the gate assembly 64 define a channel 178 that receives the flexible body 68 of the drive assembly 60. When the first passive articulation link 56 is retracted in the direction indicated by arrow "B" in FIG. 21, the cam surface 126 of the first passive articulation link 56 engages the engagement surface 182 of the gate assembly 64 to pivot the gate assembly 64 about the pivot members 180 in the direction indicated by arrow "C" in FIG. 21. As the gate assembly 64 pivots about the pivot members 180, the gate assembly 64 engages the flexible body 68 of the drive assembly 60 to urge the flexible body 68 towards the first active articulation link 52. This increases the bending radius of the flexible body 68 of the drive assembly 60 by relocating the position of the flexible body 68 in a direction opposite to the direction of articulation of the tool assembly 16. As can be seen in FIG. 21, the cam surface 106 of the articulation link 52 provides added support to the outer surface of the flexible body 68 of the drive assembly 60 to prevent buckling of the flexible body 68 when the tool assembly 16 is articulated.

As shown in FIG. 23, as the active articulation link 52 moves distally towards the mounting assembly 50, the hook 108 on the distal portion of the first active articulation link 52 engages the internal finger 81 of the mounting assembly 50 to urge the mounting assembly 50 in the direction of articulation.

When the first active articulation link 52 moves proximally as shown in FIG. 21, the bushing engagement surface 118 of the first active articulation link 52 engages and urges the slide member 142 distally in the direction indicated by arrow "K" against the urging of the springs 144 to compress the springs 144. As described in detail in the '703 application, the spring force of the springs 144 urges the slide member 142 proximally to urge the first active articulation link 52 towards a position in which the mounting assembly 50 is in a non-articulated position.

Figure 24:
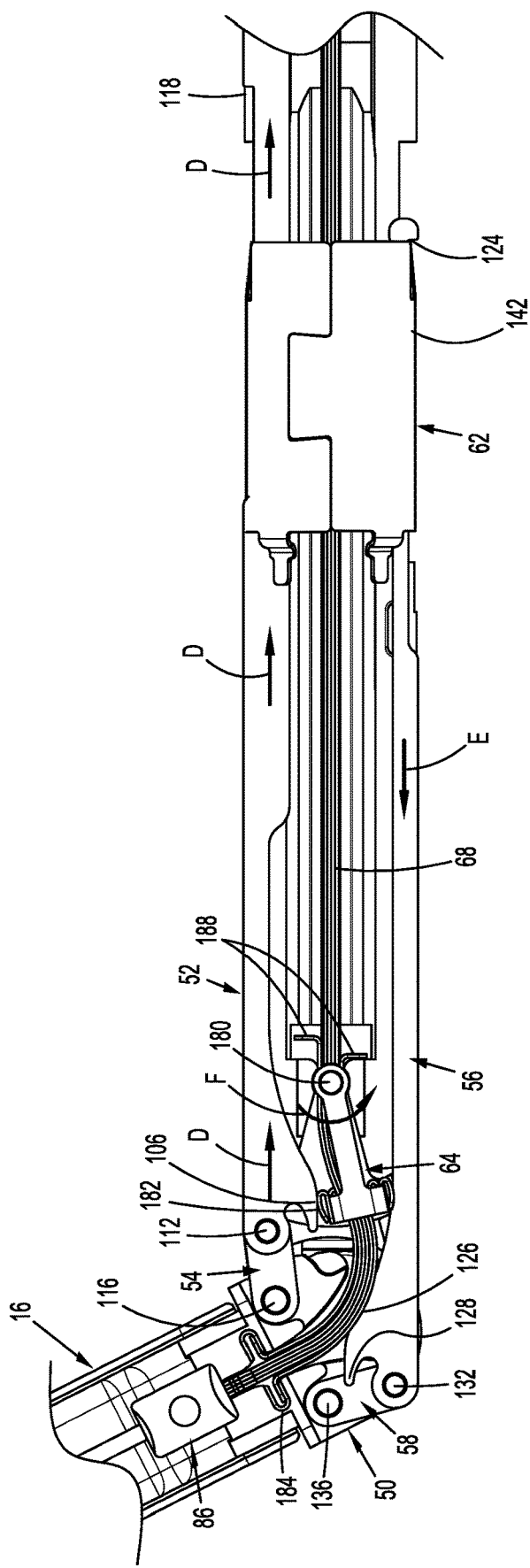
FIG. 24 is a top view of the proximal end of the tool assembly and the distal end of the proximal body portion with the tool assembly in an articulated position.

Referring to FIG. 24, when the active articulation link 52 is retracted in the direction indicated by arrows "D" by actuating the drive mechanism in the adapter assembly 14 (FIG. 1), the first active articulation link 52 retracts the second active articulation link 54 to pivot the tool assembly 16 in an opposite direction about the pivot axis "Y" (FIG. 19). As the tool assembly 16 pivots about the pivot axis "Y" (FIG. 19), the second passive articulation link 58 is moved distally and pivoted about the pivot member 136 of the mounting assembly 50. As the second passive articulation link 58 is moved distally, the first passive articulation link 56 which is pivotally coupled to the second passive articulation link 58 also moves distally in the direction indicated by arrow "E".

When the tool assembly 16 is pivoted about the pivot axis "Y", the flexible body 68 of the drive assembly 60 bends about the pivot axis "Y". As discussed above, the gates 170, 172 (FIG. 14) of the gate assembly 64 define a channel 178 that receives the flexible body 68 of the drive assembly. When the first active articulation link 52 is retracted in the direction indicated by arrow "D" in FIG. 24, the cam surface 106 of the first active articulation link 52 engages the engagement surface 182 of the gate assembly 64 to pivot the gate assembly 64 about the pivot members 180 in the direction indicated by arrow "F". As the gate assembly 64 pivots about the pivot members 180, the gate assembly 64 engages the flexible body 68 of the drive assembly 60 to urge the flexible body 68 towards the first passive articulation link 52. This increases the bending radius of the flexible body 68 of the drive assembly 60 by relocating the position of the flexible body 68 in a direction opposite to the direction of articulation of the tool assembly 16. Although not shown in FIG. 24, the cam surface 126 of the first passive articulation link 56 supports the outer surface of the blowout plate 184 to provide added support for the flexible body 68 of the drive assembly 60 to prevent buckling of the flexible body 68 when the tool assembly 16 is articulated.

As the first passive articulation link 56 moves distally towards the mounting assembly 50, the hook 128 on the distal portion of the first passive articulation link 56 engages the internal finger 81 of the mounting assembly 50 to urge the mounting assembly 50 in the direction of articulation.

When the first passive articulation link 56 moves distally, the bushing engagement surface 124 of the first passive articulation link 52 engages and urges the slide member 142 against the urging of the springs 144 (FIG. 10) to compress the springs 144. As described in detail in the '703 application, the spring force of the springs 144 urges the slide member 142 proximally to urge the first passive articulation link 56 proximally towards a position in which the mounting assembly 50 is in a non-articulated position.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
a body portion including a housing, a mounting assembly, a drive assembly, an articulation assembly, and a gate assembly, the housing including a proximal portion and a distal portion, the mounting assembly being pivotably supported on the distal portion of the housing about a pivot axis between a non-articulated position and an articulated position, the drive assembly including a flexible body having a working end, the drive assembly being movable within the housing from a retracted position to an advanced position, the articulation assembly including an active articulation link having a proximal portion and a distal portion having a cam surface, the distal portion of the active articulation link being coupled to the mounting assembly and movable between retracted and advanced positions to pivot the mounting assembly about the pivot axis, the gate assembly defining a channel, the flexible body of the drive assembly extending through the channel of the gate assembly, wherein the cam surface of the active articulation link is positioned to engage the gate assembly when the active articulation link moves from its advanced position to its retracted position to move the gate assembly to a position to bend the flexible body of the drive assembly.

2. The stapling device of claim 1, wherein the gate assembly is pivotably supported within the housing.

3. The stapling device of claim 2, wherein the gate assembly includes an upper gate and a lower gate.

4. The stapling device of claim 3, wherein each of the upper and lower gates includes an elongate body and a U-shaped member, wherein the U-shaped members of the upper and lower gates define the channel.

5. The stapling device of claim 4, wherein the elongate body of each of the upper and lower gates includes a pivot member, the pivot members pivotably connecting the upper and lower gates within the housing.

6. The stapling device of claim 5, wherein each of the U-shaped members of the upper and lower gates includes an engagement member, the active articulation link being positioned to engage one of the engagement members of the upper or lower gates.

7. The stapling device of claim 6, wherein the articulation link includes a passive articulation link, the passive articulation link having a distal portion coupled to the mounting assembly such that pivotal movement of the mounting assembly about the pivot axis causes movement of the passive articulation link between retracted and advanced positions.

8. The stapling device of claim 7, further including a blowout plate supported on each side of the elongate body of the drive assembly, each of the blowout plates having a distal end supported on the mounting assembly at a position distally of the pivot axis and a proximal end supported within the housing proximally of the pivot axis.

9. The stapling device of claim 7, further including a stabilization mechanism, the stabilization mechanism being engaged with the active and passive articulation links and being configured to urge the mounting assembly to the non-articulated position.

10. The stapling device of claim 7, wherein the distal portion of the active articulation link and the passive articulation link each include a hook and the mounting assembly includes fingers, the hooks being positioned to engage a respective one of the fingers when the respective active and passive articulation links are moved towards the advanced position to assist in articulation of the mounting assembly.

11. The stapling device of claim 7, wherein the active articulation link includes a first active articulation link and a second active articulation link that is pivotably coupled to the first active articulation link, and the passive articulation link includes a first passive articulation link and a second passive articulation link that is pivotably coupled to the first passive articulation link.

12. The stapling device of claim 1, further including a stabilization mechanism engaged with the articulation assembly, the stabilization mechanism being positioned to urge the mounting assembly to the non-articulated position.

13. The stapling device of claim 1, further including a tool assembly supported on the mounting assembly.

14. The stapling device of claim 13, wherein the tool assembly includes a cartridge assembly and an anvil assembly.

15. The stapling device of claim 14, wherein the tool assembly is configured to receive the working end of the device assembly.

16. The stapling device of claim 1, wherein the distal portion of the active articulation link includes a hook and the mounting assembly includes a finger, and the hook is positioned to engage the finger when the active articulation link is moved towards the advanced position to assist in articulation of the mounting assembly.

17. The stapling device of claim 16, wherein the active articulation link includes a first active articulation link and a second active articulation link that is pivotably coupled to the first active articulation link.

* * * * *